US009962077B2

(12) United States Patent
Farrer et al.

(10) Patent No.: US 9,962,077 B2
(45) Date of Patent: *May 8, 2018

(54) SYSTEM AND METHOD FOR CORNEAL TOPOGRAPHY WITH FLAT PANEL DISPLAY

(71) Applicant: AMO WaveFront Sciences, LLC, Santa Ana, CA (US)

(72) Inventors: Stephen W. Farrer, Albuquerque, NM (US); W. Shea Powers, Albuquerque, NM (US); Daniel R. Neal, Tijeras, NM (US); Larry B. Voss, Tijeras, NM (US)

(73) Assignee: AMO Wavefront Sciences, LLC, Albuquerque, NM (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/476,670

(22) Filed: Mar. 31, 2017

(65) Prior Publication Data
US 2017/0202455 A1    Jul. 20, 2017

Related U.S. Application Data

(63) Continuation-in-part of application No. 14/788,569, filed on Jun. 30, 2015, now Pat. No. 9,615,739.
(Continued)

(51) Int. Cl.
*A61B 3/10* (2006.01)
*A61B 3/107* (2006.01)
(Continued)

(52) U.S. Cl.
CPC .............. *A61B 3/107* (2013.01); *A61B 3/005* (2013.01); *A61B 3/0025* (2013.01); *A61B 3/14* (2013.01)

(58) Field of Classification Search
CPC .. A61B 3/14; A61B 3/13; A61B 3/107; A61B 3/0041
(Continued)

(56) References Cited

U.S. PATENT DOCUMENTS

| 4,993,826 A | 2/1991 | Yoder, Jr. |
| 5,062,702 A | 11/1991 | Bille |

(Continued)

FOREIGN PATENT DOCUMENTS

| CA | 2538157 A1 | 3/2005 |
| WO | 9806320 A1 | 2/1998 |
| WO | 2014072342 A1 | 5/2014 |

OTHER PUBLICATIONS

Gatabi J.R., et al., "Three Dimensional Surface Topography Using LCD Pattern Transfer Method," American Physical Society, Joint Spring 2012 Meeting of the Texas Sections of the APS and AAPT and Zone 13 of the SPS, Mar. 22-24, 2012, vol. 57 (2), Abstract #E1.006.
(Continued)

*Primary Examiner* — Hung Dang
(74) *Attorney, Agent, or Firm* — Johnson & Johnson Surgical Vision, Inc.

(57) ABSTRACT

A corneal topographer includes: a flat panel display configured to display a light pattern and to project the light pattern onto a cornea of an eye disposed on a first side of the flat panel display; an optical system disposed on a second side of the flat panel display, the optical system being configured to receive and process reflected light from the cornea that passes through the flat panel display from the cornea to the optical system; a camera configured to receive the processed reflected light from the optical system and to capture therefrom a reflected light pattern from the cornea produced in response to the projected light pattern; and one or more processors configured to execute an algorithm to compare
(Continued)

the projected light pattern to the reflected light pattern from the cornea, and to produce a topographic map of the cornea based on a result of the comparison.

24 Claims, 11 Drawing Sheets

Related U.S. Application Data

(60) Provisional application No. 62/019,763, filed on Jul. 1, 2014.

(51) Int. Cl.
*A61B 3/00* (2006.01)
*A61B 3/14* (2006.01)

(58) Field of Classification Search
USPC ....... 351/212, 211, 200, 205, 206, 246, 213, 351/214, 221
See application file for complete search history.

(56) References Cited

U.S. PATENT DOCUMENTS

| 5,526,072 | A | 6/1996 | El Hage |
| 5,684,562 | A | 11/1997 | Fujieda |
| 6,224,213 | B1 | 5/2001 | Kobayashi |
| 6,601,956 | B1 | 8/2003 | Jean et al. |
| 6,634,750 | B2 | 10/2003 | Neal et al. |
| 6,634,752 | B2 | 10/2003 | Curatu |
| 6,974,215 | B2 | 12/2005 | Hayashi |
| 7,976,163 | B2 | 7/2011 | Campbell et al. |
| 8,602,033 | B2 | 12/2013 | Jones et al. |
| 8,740,795 | B2 | 6/2014 | Norris et al. |
| 9,615,739 | B2 * | 4/2017 | Farrer .................. A61B 3/107 |
| 2013/0070203 | A1 | 3/2013 | Michaels et al. |

OTHER PUBLICATIONS

International Search Report and Written Opinion for Application No. PCT/US2015/038702, dated Oct. 6, 2015, 10 pages.

Mejia-Barbosa Y., et al., "Object Surface for Applying a Modified Hartmann Test to Measure Corneal Topography," Applied Optics, 2001, vol. 40 (31), pp. 5778-5786.

* cited by examiner

SYSTEM AND METHOD FOR CORNEAL TOPOGRAPHY WITH FLAT PANEL DISPLAY

CROSS-REFERENCE TO RELATED APPLICATION

This application is a continuation application under 35 USC § 120 of U.S. patent application Ser. No. 14/788,569, filed Jun. 30, 2015, now allowed, which claims priority to U.S. Provisional Application No. 62/019,763 filed on Jul. 1, 2014. The disclosures of the above two applications are hereby incorporated by reference in their entireties.

FIELD OF THE INVENTION

Embodiments of this invention generally pertain to the field of vision diagnostics, and particularly to systems and methods for corneal topography.

BACKGROUND

Ocular aberrations typically produce unwanted results in the form of bad eyesight. Accurately characterizing these aberrations can lead to appropriate prescriptions and methods for treatment. Since typically 60-70% of ocular aberrations result from imperfections in the cornea, the ability to determine the corneal topography of an eye is highly desirable. Corneal topography is typically determined with a device called a corneal topographer. A variety of corneal topographers are known in the art, examples of which are disclosed in U.S. Pat. Nos. 5,062,702, 6,634,752, and 7,976,163, which are herein incorporated by reference.

One type of corneal topographer employs a "Placido disk" system. A Placido disk system consists of a series of concentric illuminated rings that are reflected off the cornea and viewed with a detector array, such as a charge-coupled device (CCD) or a video camera. Because of its simplicity, the Placido disk topography system has been widely used for measuring corneal topography. A key part of this system is the object or device surface with rings, as well as the spatial distribution and the width of these rings on the surface of the device. The location and width of the rings on the device are computed in such a way that the image of the rings reflected off a reference sphere is a uniform distribution of rings, i.e., rings equally spaced, and all with the same width. The radius of curvature of the reference sphere is made equal to the mean radius of the cornea (about 7.8 mm). Then, the image of the rings reflected off a cornea with aberrations will constitute of distorted rings, and from this distortion, one can obtain the shape of the cornea.

Many variations on the Placido disk approach for corneal topography measurements have been developed over the years, examples of which are disclosed in U.S. Pat. Nos. 4,993,826 and 6,601,956, and by Yobani Mejía-Barbosa et al., "Object surface for applying a modified Hartmann test to measure corneal topography," APPLIED OPTICS, Vol. 40, No. 31 (Nov. 1, 2001) ("Mejía-Barbosa"). Mejía-Barbosa is incorporated herein by reference for all purposes as if fully set forth herein.

One problem in many Placido disk type corneal topographers is alignment error, which is commonly referred to as a vertex error between the corneal surface vertex and the design corneal vertex plane. More specifically, to make accurate calculations of corneal topography, the device expects the cornea to be located at a particular location long the optical axis of the system with respect to the Placido light sources. If an actual cornea that is being measured is "too close" or "too far" from the instrument or device, vertex error that will produce inaccurate corneal topography results, unless the vertex error can be determined and factored into the corneal topography calculations.

Another problem with Placido disk type corneal topographers is that the data is obtained from analysis of a series of projected rings. In other words, a radial position of the detected ring is compared to a reference position and the comparison is used to determine the corneal shape. This, however, only provides radial deviations. While these are azimuthally resolved, they do not provide an adequate measure of the "skew" rays, i.e., those rays which would be deflected in an azimuthal direction. This is an inherent limitation for a system using Placido rings topographers. The limitation is especially significant considering that astigmatism, one of the major classes of ocular aberrations, is known to generate significant skew rays.

Instead of using concentric rings, other corneal topographers have been developed that employ a light pattern comprising an array of light sources provided on a surface having the shape of a conical frustrum, a hemisphere or other modified sphere, or an elongated oval and the like. This light pattern is projected onto the cornea of the eye, and corneal topography is determined by observing the reflected light pattern of reflected spots from the cornea, and comparing this pattern to the projected light pattern from the light sources. In such a system and method of corneal topography, it is important to match each reflected light spot in the reflected light pattern to the projected light source which produced it so as to make an accurate comparison. This can be difficult for corneas with highly aberrated topographies. But, such matching may be improved if the pattern of projected light sources could be reconfigured dynamically to create easily recognizable fiducials, and/or to increase the density of the reflected light sources in areas which map to more highly aberrated portions of the cornea.

Unfortunately, in many known corneal topographers that employ a pattern of projected light sources, the pattern cannot easily be reconfigured to change the colors, positions, shapes, sizes, and localized densities of the projected light spots in the pattern.

Furthermore, whether they employ Placido disks or an array of light sources, these known conical topographers employ relatively complex light generating structures, which typically do not easily lend themselves to small, portable, and relatively inexpensive corneal topography constructions that might be desirable for providing corneal topography service to poor, remote, and rural populations.

SUMMARY OF THE INVENTION

Accordingly, it would be desirable to provide a system and method of corneal topography of an eye so as to obviate one or more problems due to limitations and disadvantages of the related art.

In one aspect of the invention, an apparatus for corneal topography comprises: a flat panel display configured to display a light pattern and to project the light pattern onto a cornea of an eye disposed on a first side of the flat panel display; an optical system disposed on a second side of the flat panel display, the optical system being configured to receive and process reflected light from the cornea that passes through the flat panel display from the cornea to the optical system; and a camera configured to receive the processed reflected light from the optical system and to capture therefrom a reflected light pattern from the cornea produced in response to the projected light pattern.

In some embodiments, the apparatus further comprises one or more processors configured to execute an algorithm to compare the projected light pattern to the reflected light pattern from the cornea, and to produce a topographic map of the cornea based on a result of the comparison.

In some embodiments, the flat panel display is a transparent flat panel display, wherein the reflected light from the cornea passes through the transparent flat panel display to the optical system.

In some embodiments, the flat panel display has an aperture passing therethrough, wherein the reflected light from the cornea passes through the aperture to the optical system.

In some embodiments, the projected light pattern comprises a pattern of projected light spots and the reflected light pattern from the cornea comprises a pattern of reflected light spots.

In some embodiments, the projected light spots are colored light spots, and various projected light spots have different colors to facilitate association of the reflected light spots with the projected light spots from which they were generated.

In some versions of these embodiments, the apparatus is configured to dynamically adjust the colors of the projected light spots to facilitate association of the reflected light spots with the projected light spots from which they were generated.

In some versions of these embodiments, the projected light spots each have a size and shape, and at least one of the size and shape of at least two of the projected light spots differ from each other to facilitate association of the reflected light spots with the projected light spots from which they were generated.

In some versions of these embodiments, the apparatus is configured to dynamically adjust at least one of the size and shape of the projected light spots to facilitate association of the reflected light spots with the projected light spots from which they were generated.

In some versions of these embodiments, the apparatus is configured to dynamically adjust a local density of the projected light spots to facilitate association of the reflected light spots with the projected light spots from which they were generated to facilitate production of the topographic map of the cornea.

In another aspect of the invention, a method for corneal topography comprises: projecting a light pattern from a flat panel display onto a cornea of an eye disposed on a first side of the flat panel display; receiving and optically processing reflected light from the cornea that passes through the flat panel display via an optical system disposed on a second side of the flat panel display; receiving at a camera the optically processed reflected light from the optical system; capturing from processed reflected light via the camera a reflected light pattern from the cornea produced in response to the projected light pattern; comparing the projected light pattern to the reflected light pattern from the cornea; and producing a topographic map of the cornea based on a result of the comparison.

In some embodiments, the flat panel display is a transparent flat panel display, and the method further comprises passing the reflected light from the cornea through the transparent flat panel display to the optical system.

In some embodiments, the flat panel display has an aperture passing therethrough, and the method further comprises passing the reflected light from the cornea through the aperture to the optical system.

In some embodiments, the projected light pattern comprises a pattern of projected light spots and the reflected light pattern from the cornea comprises a pattern of reflected light spots.

In some versions of these embodiments, the projected light spots are colored light spots, and various projected light spots have different colors to facilitate association of the reflected light spots with the projected light spots from which they were generated.

In some versions of these embodiments, the method further comprises dynamically adjusting the colors of the projected light spots to facilitate association of the reflected light spots with the projected light spots from which they were generated.

In some versions of these embodiments, the projected light spots each have a size and shape, and at least one of the size and shape of at least two of the projected light spots differ from each other to facilitate association of the reflected light spots with the projected light spots from which they were generated.

In some versions of these embodiments, the method further comprises dynamically adjusting at least one of the size and shape of the projected light spots to facilitate association of the reflected light spots with the projected light spots from which they were generated.

In some versions of these embodiments, the method further comprises dynamically adjusting a local density of the projected light spots to facilitate association of the reflected light spots with the projected light spots from which they were generated to facilitate production of the topographic map of the cornea.

In yet another aspect of the invention, an apparatus for corneal topography comprises: a portable computing device, comprising: a housing; a flat panel display connected to the housing and configured to display a light pattern thereon and to project the light pattern onto a cornea of an eye disposed on a first side of the flat panel display, and one or more processors disposed within the housing of the portable computing device; an optical system disposed on a second side of the transparent flat panel display, configured to receive and process reflected light from the cornea that passes through the flat panel display; and a camera configured to receive the processed reflected light from the optical system and to capture therefrom a reflected light pattern from the cornea produced in response to the projected light pattern, wherein the one or more processors are configured to receive image data from the camera and to process the image data to produce a topographic map of the cornea.

In some embodiments, the portable computing device comprises one of a smart phone and a tablet computer.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE DRAWINGS

The novel features of the invention are set forth with particularity in the appended claims. A better understanding of the features and advantages of the present invention will be obtained by referring to the following detailed description that sets forth illustrative embodiments using principles of the invention, as well as to the accompanying drawings of which:

DETAILED DESCRIPTION

As discussed above, it would be desirable to provide a system and method for corneal topography which may have some advantages compared to existing systems and methods. The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

Figure 1A:
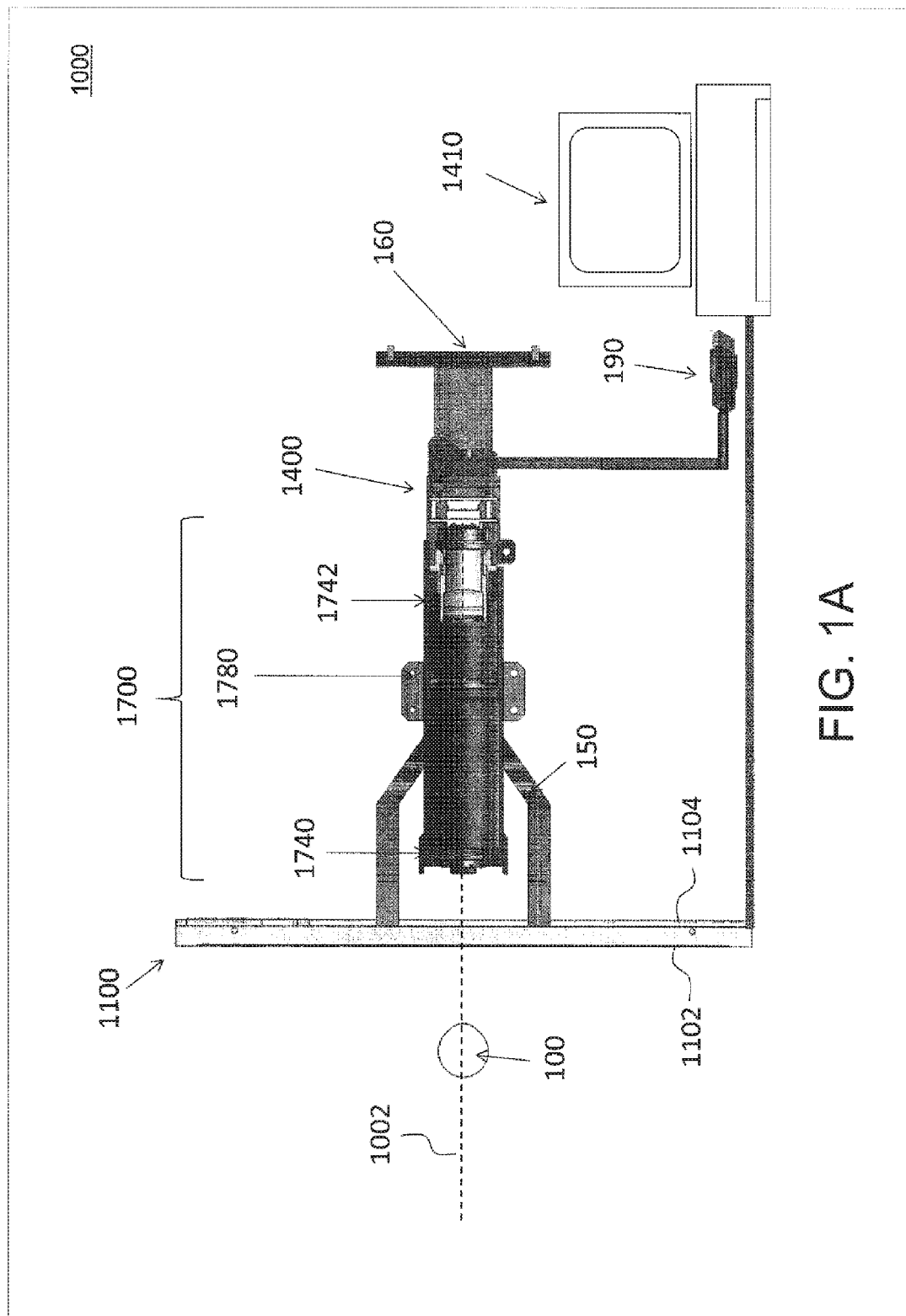
FIG. 1A shows a side view of a first embodiment of a system for measuring corneal topography of an eye.
Figure 1B:
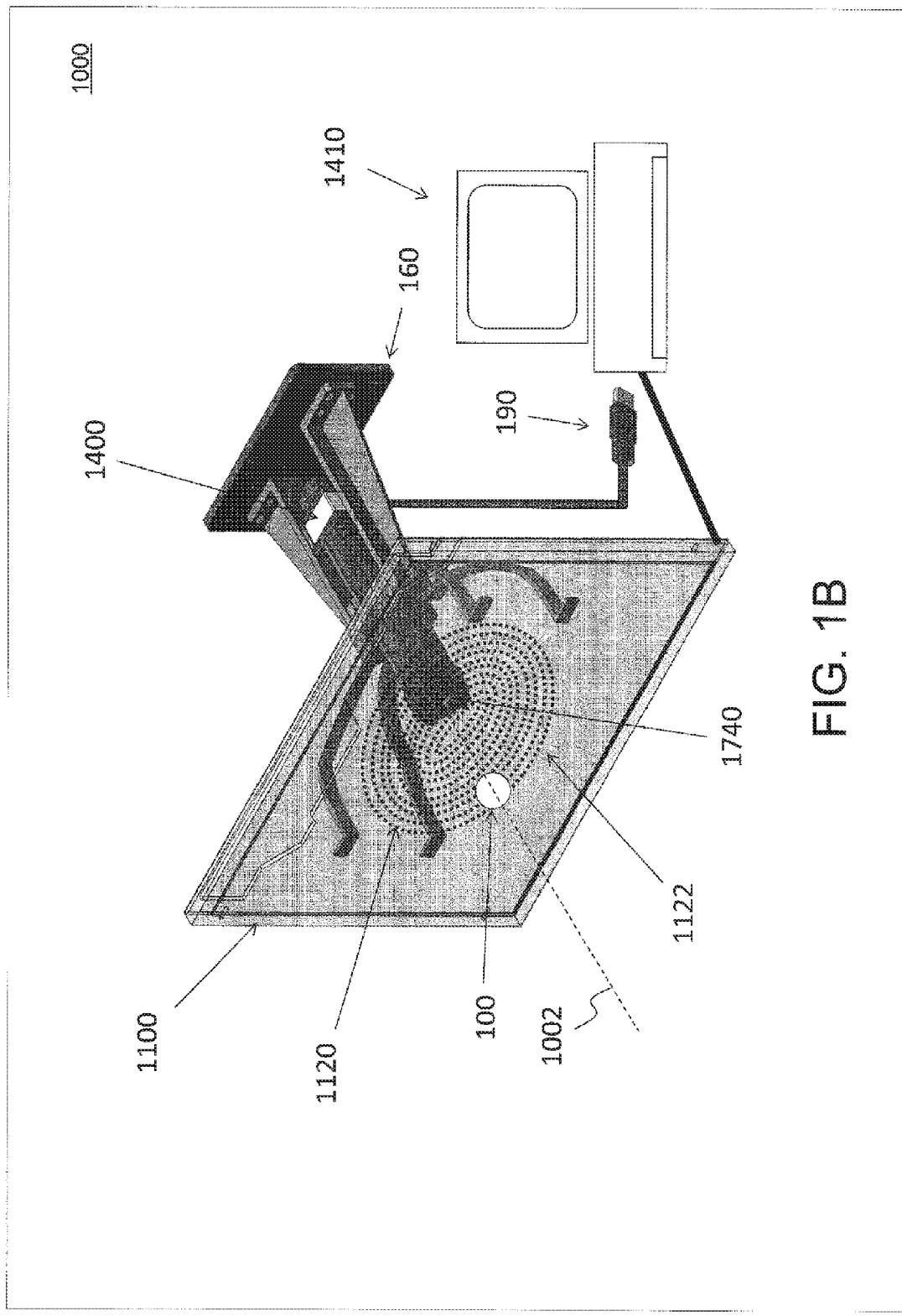
FIG. 1B illustrates a perspective view of the first embodiment of a system for measuring corneal topography of an eye.
Figure 1C:
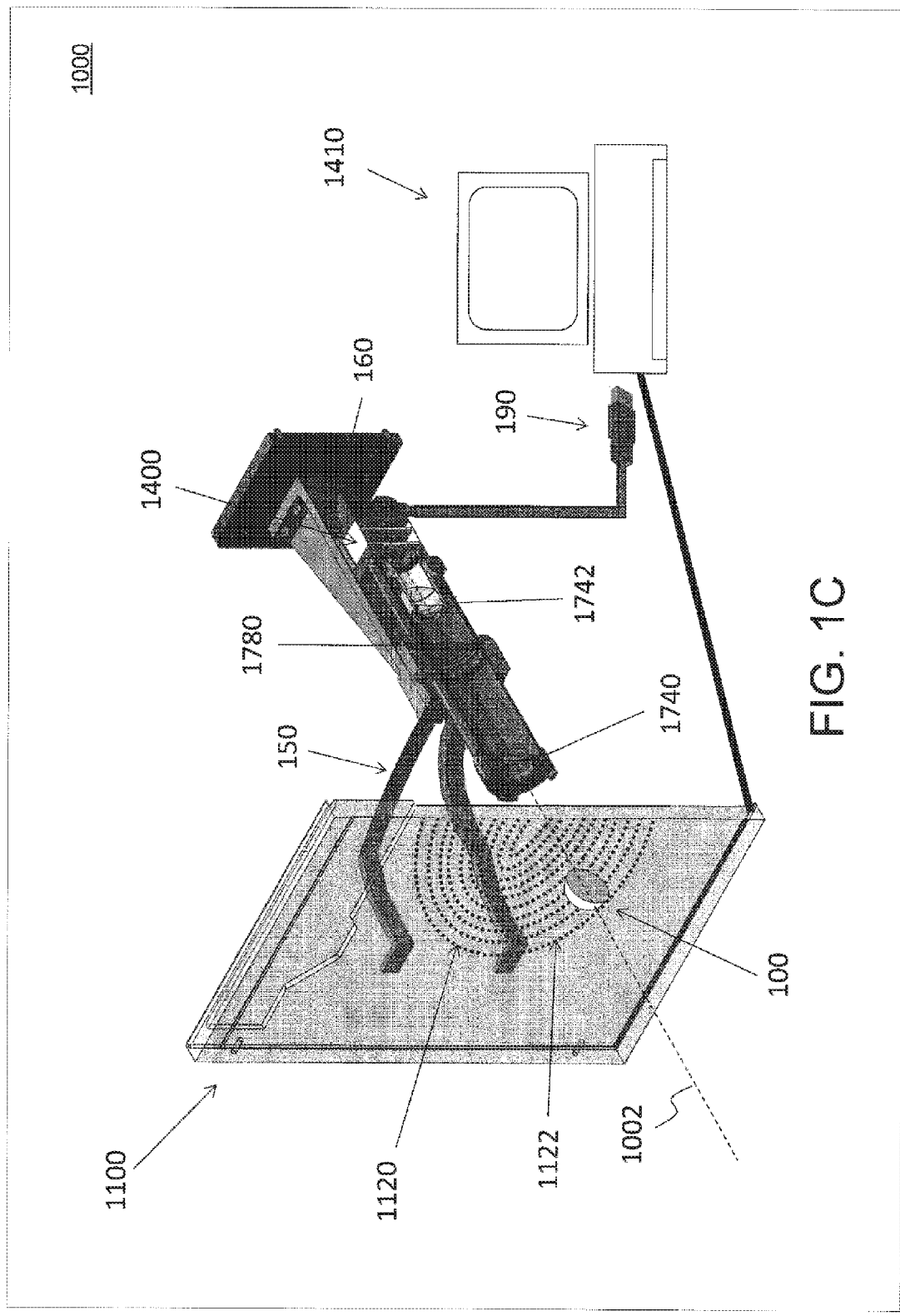
FIG. 1C illustrates a partial cutaway perspective view of the first embodiment of a system for corneal topography of an eye.

FIG. 1A shows a side view of a first embodiment of a system 1000 for measuring corneal topography of an eye 100. FIG. 1B illustrates a perspective view of system 1000, and FIG. 1C illustrates a partial cutaway perspective view of system 1000.

System 1000 comprises a flat panel display 1100 having a first surface 1102 and a second surface 1104; a camera or detector array 1400; and an optical system 1700 disposed on a along a central axis 1002 passing flat panel display 1100. The eye 100 is disposed opposite first surface 1102 on a first side of flat panel display 1100 and optical system 1700 disposed opposite second surface 1102 on a second side of flat panel display 1100. Optical system 1700 comprises a first optical element (e.g., a lens) 1740, a structure including a telecentric aperture (or stop) 1780, and a second optical element (e.g., lens) 1742. It will be appreciated by those of skill in the art that the lenses 1742, 1744, or any of the other lenses discussed herein, may be replaced or supplemented by another type of converging or diverging optical element, such as a diffractive optical element. In some embodiments, optical system 1700 may be mounted or provided in a tube which is mounted to flat panel display 1100 by a mounting bracket 150, and may be mounted to an instrument chassis or body via a mounting plate 160.

Camera 1400 may comprise a charge coupled device (CCD), a complementary metal oxide semiconductor (CMOS) array, or another electronic photosensitive device.

System 1000 also one or more processors 1410 which may be connected to an output of camera 1400 via a connector 190. Processor(s) 1410 may have associated therewith volatile and/or nonvolatile memory or other storage media, an operating system, executable code, a user interface including for example, keyboard, mouse, trackball, touchscreen, etc.), and like components of known processor(s). In some embodiments, processor(s) 1410 may be embodied in a personal computer. Some embodiments of a system 1000 for measuring corneal topography of an eye 100 may output data from connector 190 to one or more external processor(s) 1410 which may be provided separately from system 1000. In that case, processor(s) 1410 may be embodied in a portable device such as a tablet computing device or a smartphone which can be connected to the output of camera 1400 via connector 190.

Beneficially, in some embodiments system 1000 may further include other elements not shown in FIGS. 1A-1C, which may include a fixation target, a movable patient alignment stage, one or more eye illumination devices, a wavefront aberrometer (for example including a Shack-Hartmann wavefront sensor), a user interface etc.

In system 1000, flat panel display 1100 comprises a transparent color display device, such as a transparent color liquid crystal display (LCD) device. Beneficially, flat panel display 1100 may include other standard display components, such as driver circuitry, buffer memory, etc.

System 1000 measures the curvature and shape of the cornea of eye 100. Light for this measurement is provided by light spots 1122. As can be seen in FIGS. 1B and 1C, in operation flat panel display 1100 produces a light pattern 1120 comprising a plurality of individually controllable light spots 1122 by illuminating corresponding pixels of flat panel display 1100. Here, a "light spot" means an area of locally increased electromagnetic radiation in or near the visible band of the electromagnetic spectrum, for example, in the infrared, near infrared, or ultraviolet bands of electromagnetic radiation. As used herein, the term "light" means electromagnetic radiation in or near the visible band of the electromagnetic spectrum, for example, in the infrared, near infrared, or ultraviolet bands of electromagnetic radiation.

In normal use, an operator may adjust a position or alignment of system 1000 in XY and Z directions to align the patient according to camera 1400. At this time, an operator may see an image of the iris of eye 100. The cornea generally magnifies and slightly displaces the image from the physical location of the iris. So the alignment may actually be done to the entrance pupil of the eye.

Light spots 1122 of light pattern 1120 are projected from flat panel display 1100 onto the cornea of eye 100, which is disposed on the first side of flat panel display 1100. In turn, cornea 100 reflects the light spots generally back toward flat panel display 1100, as described in greater detail below. Images of the individual projected light spot 1122 appear as reflected light spots on camera 1400, which is disposed on the second side of flat panel display 1100.

In some embodiments, flat panel display 1100 may include an input for receiving display data and control signals from an external processor, which may be processor 1410, for generating the projected light pattern 1120. Beneficially, flat panel display 1100 may be controlled to change the colors, positions, shapes, sizes, and localized densities of projected light spots 1122 in virtually any way desired, for example in response to data and control signals received from processor 1410, as described in greater detail below. In particular, the colors, positions, shapes, sizes, and localized densities of projected light spots 1112 may be varied for corneal topography of eye 100, in particular to facilitate matching of projected light spots 1122 to reflected light spots which pass through optical system 1700 and appear on camera 1400.

As noted above, cornea 100 reflects the projected light spots generally back toward flat panel display 1100.

Figure 2:
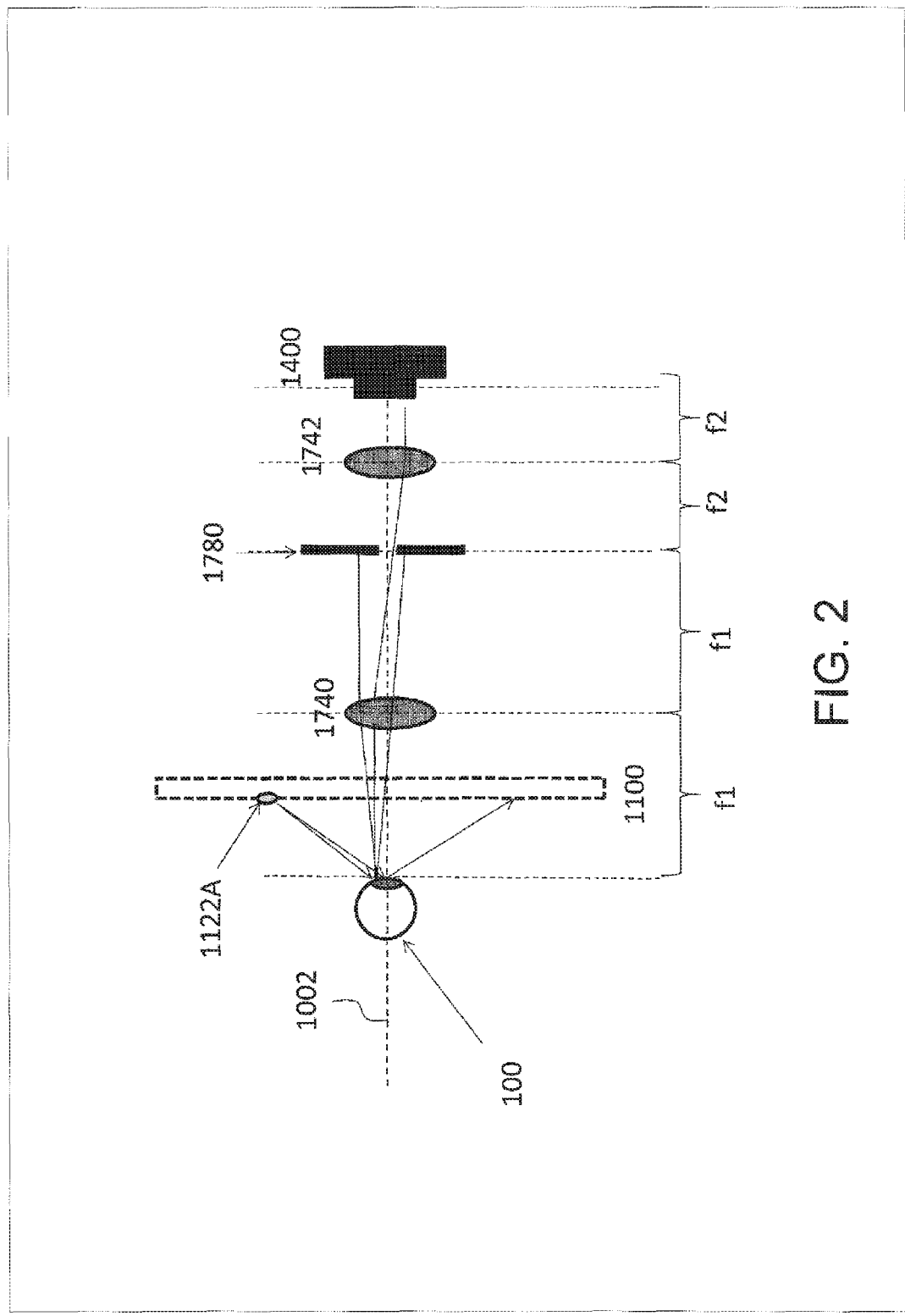
FIG. 2 illustrates rays for a projected light spot and a reflected light spot in the system of FIGS. 1A-C.

FIG. 2 illustrates rays for a projected light spot 1122A and a reflected light spot in system 1000. As shown in FIG. 2, rays of light from projected light spot 1122A which are reflected by the cornea of eye 100 back toward flat display panel 1100 at a wide range of angles. Notably, some of the rays are reflected back toward flat display panel 1100 generally along optical axis 1002 of optical system 1700, while other reflected rays diverge at a wide range of angles with respect to optical axis 1002. The structure including telecentric aperture 1780 ensures that only those reflected rays from projected light spot 1122A which return from the cornea of eye 100 along optical axis 1002, or at a narrow angle with respect to optical axis 1002, pass through optical system 700 to reach camera 1400 and thereby produce a reflected light spot at camera 1400. This same phenomenon holds true for each projected light spot 1122 of projected light pattern 1120.

The diameter of telecentric aperture 1780 may be selected to determine how much light from any particular projected light spot 1122 is sampled. If aperture 1780 is made too large, there may be too much overlap between the individual images of the individual projected light spot 1122 for accurate calculation of corneal shape. However, if aperture 1780 is made too small, not enough light reaches detector array 1400 for a usable image to form. In one embodiment, a practical size for aperture 1780 may be between 1 and 4 mm.

Figure 3:
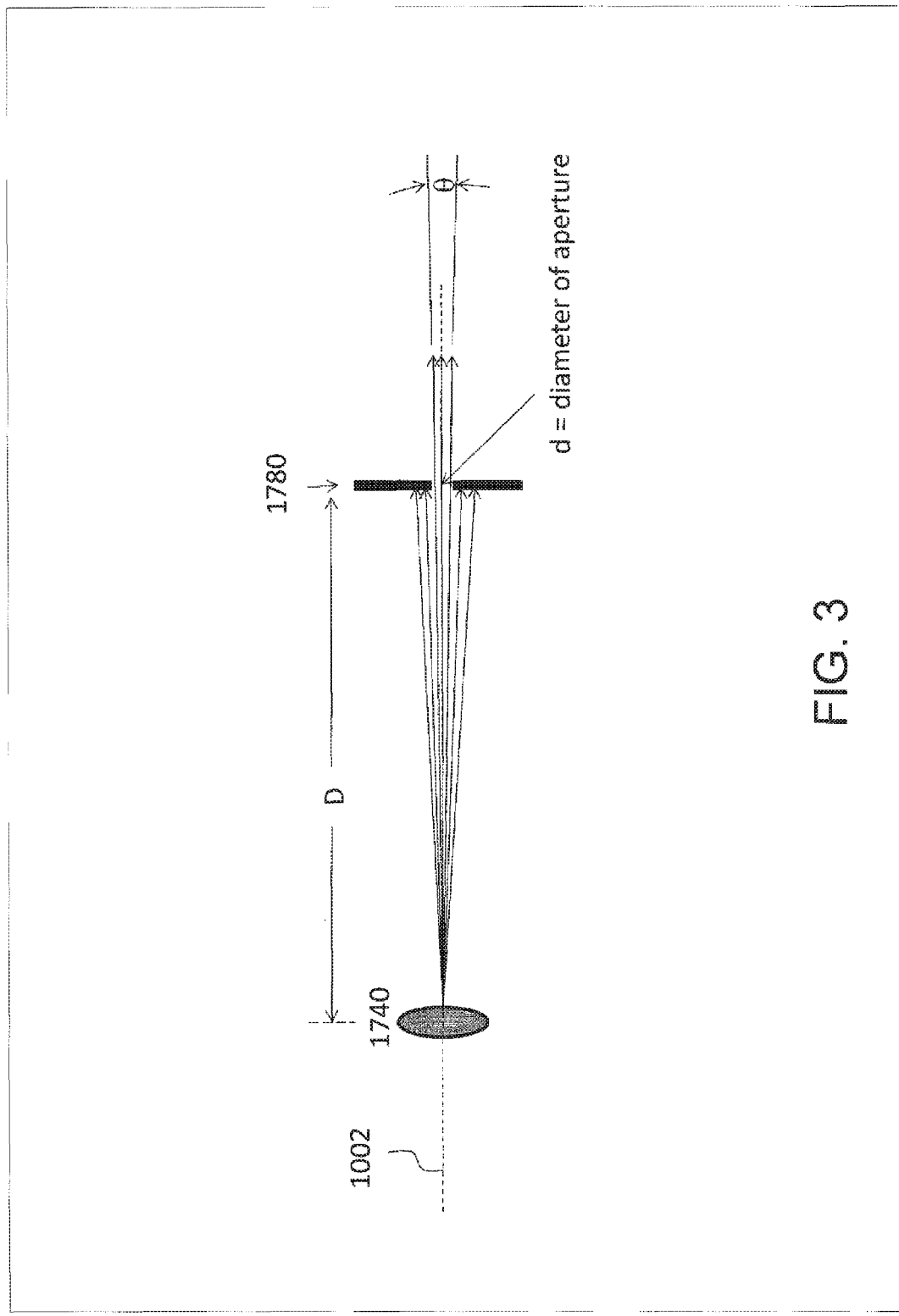
FIG. 3 illustrates rays for a reflected light spot in the system of FIGS. 1A-C.

Beneficially, aperture 1780 may be selected such that it is the only aperture that restricts how much light reaches detector array 1400. Deviations from that can result in departures from telecentricity and consequent miscalculations of the shape of the cornea FIG. 3 illustrates rays for a reflected light spot in system 1000. In FIG. 3, the diameter of telecentric aperture 1780 is denoted as "d" and the distance between first lens 1740 and telecentric aperture 1780 is denoted as "D." The aperture diameter d and the distance D determine the acceptance angle θ of light rays that will be allowed to pass through aperture 1780.

In one example embodiment, d may be 3 mm, D may be 74 mm, and in that case may be 2.35°. Because of the typical curvature of a corneal (radius of curvature~8 mm), the area that produces such a small ray bundle having an angular range of 2.35° when mapped back on to the cornea is relatively small, allowing system 1000 to image small light spots that have reflected off the cornea and traveled through telecentric aperture 1780.

Aperture 1780 may influence the operation of system 1000 in several ways.

First, the size of aperture 1780 sets the solid angle of rays that can be accepted and passed to camera 1400. This solid angle in turn sets the area of the corneal surface that is sampled by any given projected light spot 1122. This may be understood by thinking of the image of a given projected light spot 1122 to be located as a virtual image posterior to the corneal surface. Projecting forward from this spot image is a cone of rays; the solid angle that camera 1400 can "see." The intersection of this cone with the cornea surface defines the area of that surface sampled by the light source spot. So, setting the size of aperture 1780 localizes the area of the cornea that a given projected light spot 1122 samples.

Second, because the sampled area size is set by the size of aperture 1780, it sets the amount of light that any single projected light spot 1122 deposits on detector array 1400. Thus, if aperture 1780 is made too small, the spots images are too dim.

Third, the size of aperture 1780 sets the depth of focus of camera 1400. If aperture 1780 is too large and the virtual images created by the cornea lie in different planes due to the fact that the power of the cornea, i.e. its curvature, is different in different areas, it becomes hard to get all images in sharp enough focus on detector array 1400 to achieve good image processing results. This can be a problem when measuring an eye 100 which exhibits keratoconus.

Figure 4:
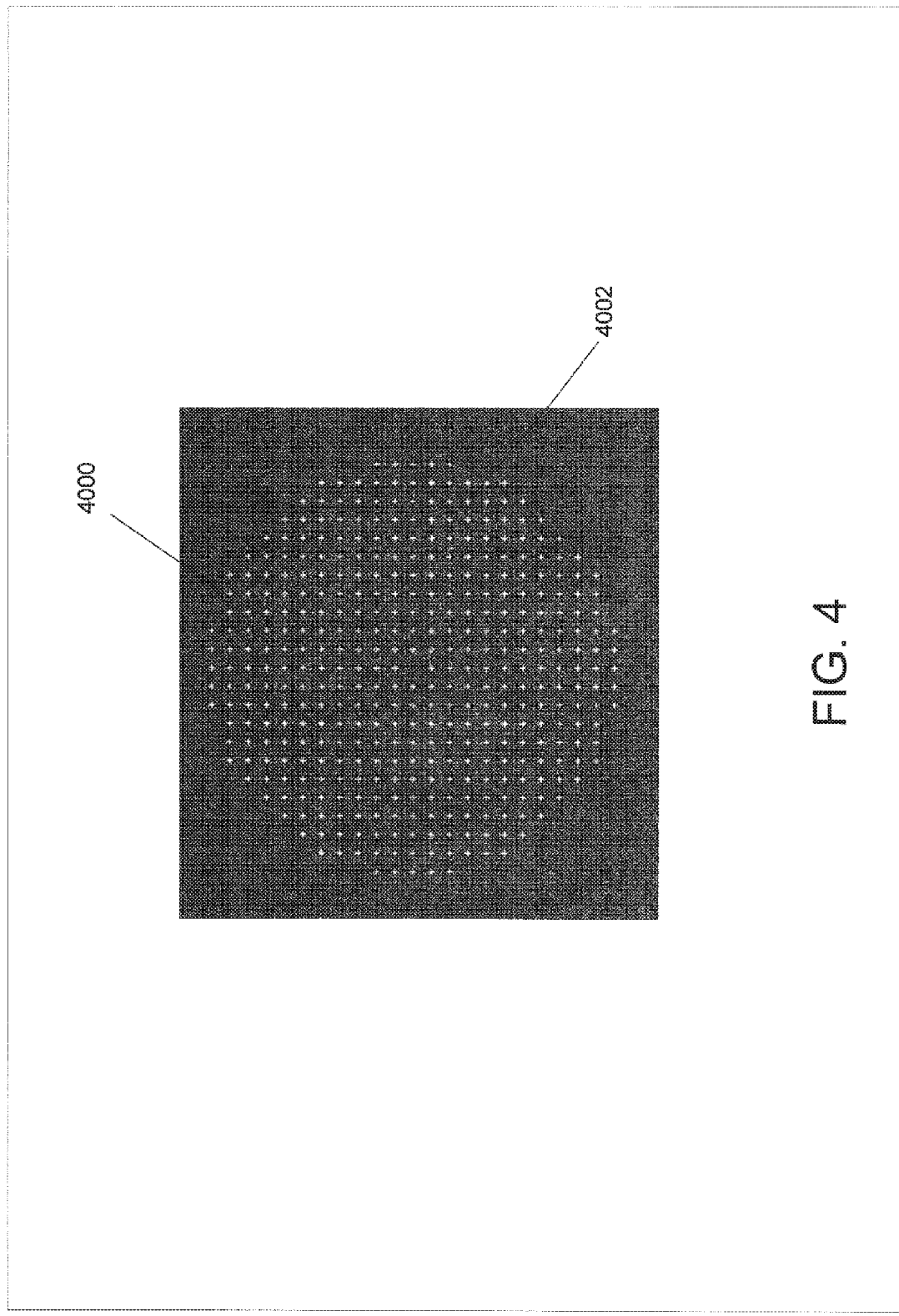
FIG. 4 illustrates an example of an idealized pattern of light spots produced on a camera or detector array in the system of FIGS. 1A-C.

FIG. 4 illustrates an example of an idealized reflected light pattern 4000 of idealized reflected light spots 4002 produced on camera 1400 in system 1000. Beneficially, idealized reflected light spots 4002 of idealized reflected light pattern 4000 may be substantially uniformly distributed at camera 1400. Idealized reflected light pattern 4000 may be a light pattern which is produced in response to projecting projected light pattern 1120 onto an ideal cornea (that is, a cornea having an ideal, or nominal shape).

There are several reasons for wanting a uniform grid produced at camera 1400. If a reference surface (e.g., an idealized cornea, a sphere with ROC=8.0 mm, etc.) could produce the pattern of FIG. 4, for example, on camera 1400, this could facilitate easier reconstruction of the corneal topography, since the expected spots for a "reference eye" will be on a grid, and small deviations might easily lead to simple reconstruction methods. Furthermore, with the spot pattern being close to a grid, the spot location algorithm becomes much simpler and might easily be tackled with a difference image calculated from an image with and without first light sources 1200 turned-on, followed by centroiding algorithms based on predefined areas of interest (AOI). An additional translation calculation might be needed prior to AOI-based centroiding to account for system misalignment.

Figure 5:
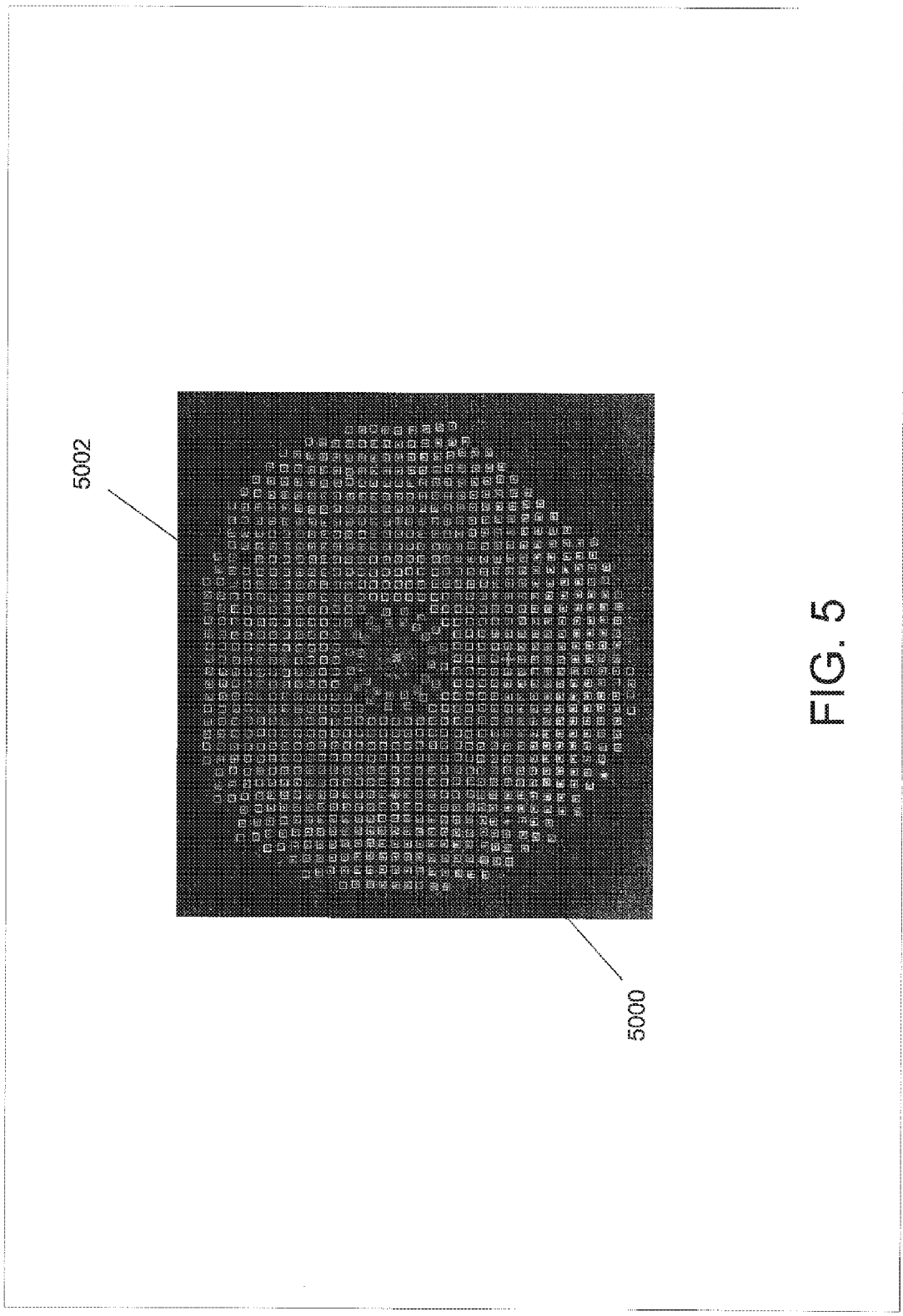
FIG. 5 illustrates an example of a non-idealized pattern of light spots produced on a camera or detector array in the system of FIGS. 1A-C.

When performing corneal topography on a real cornea, however, in general the reflected light spots do not all appear at the same locations on camera 1400 as idealized reflected light spots 4002. FIG. 5 illustrates an example of a non-idealized reflected light pattern 5000 of non-idealized reflected light spots 5002 produced on camera or detector array 1400 in system 1000.

The differences between the locations where reflected light spots 5002 appear on camera 1400 and the locations where the corresponding idealized reflected light spots 4002 from the same projected light spots 1122 would have appeared are produced by aberrations in the corneal topograph. Corneal aberrations can also change the shape of reflected light spots 5002.

Accordingly, in operation processor(s) 1410 may reconstruct the corneal topograph from the image data output by camera 1400 indicating the shapes and/or locations of reflected light spots 5002 on camera 1400, and a priori knowledge of the shapes and/or locations where the corresponding idealized reflected light spots 4002 from the same projected light spots 1122 would have appeared. Put another way, processor(s) 1410 may determine the locations and/or shapes of reflected light spots 5002 on detector array 1400, and compares these locations and/or shapes to those expected for a standard or model cornea, thereby allowing processor 1410 to determine the corneal topography of eye 100, employing one of various known algorithms. However, to employ these algorithms, the non-idealized reflected light spots 5002 should be accurately mapped to the original projected light spots 1122 which produced it.

In some embodiments, processor(s) 1410 may employ pattern recognition (correlation based) on the image data produced by camera 1400. However, when the corneal aberration is severe, it may be difficult to match reflected light spots 5002 to the projected light spots 1122 which produced them.

In some embodiments, unique fiducials associated with known light spot locations may be employed a basis for light spot association. Toward this end, beneficially, the colors, positions, shapes, sizes, and localized densities of projected light spots 1112 may be varied for corneal topography of eye 100, in particular to facilitate matching of projected light spots 1122 to reflected light spots 5002. Furthermore, the density of projected light spots 1112 corresponding to regions of high aberration in the corneal topograph may be increased dynamically and easily via flat panel display 1100 to further facilitate matching of projected light spots 1122 to reflected light spots 5002.

Figure 6:
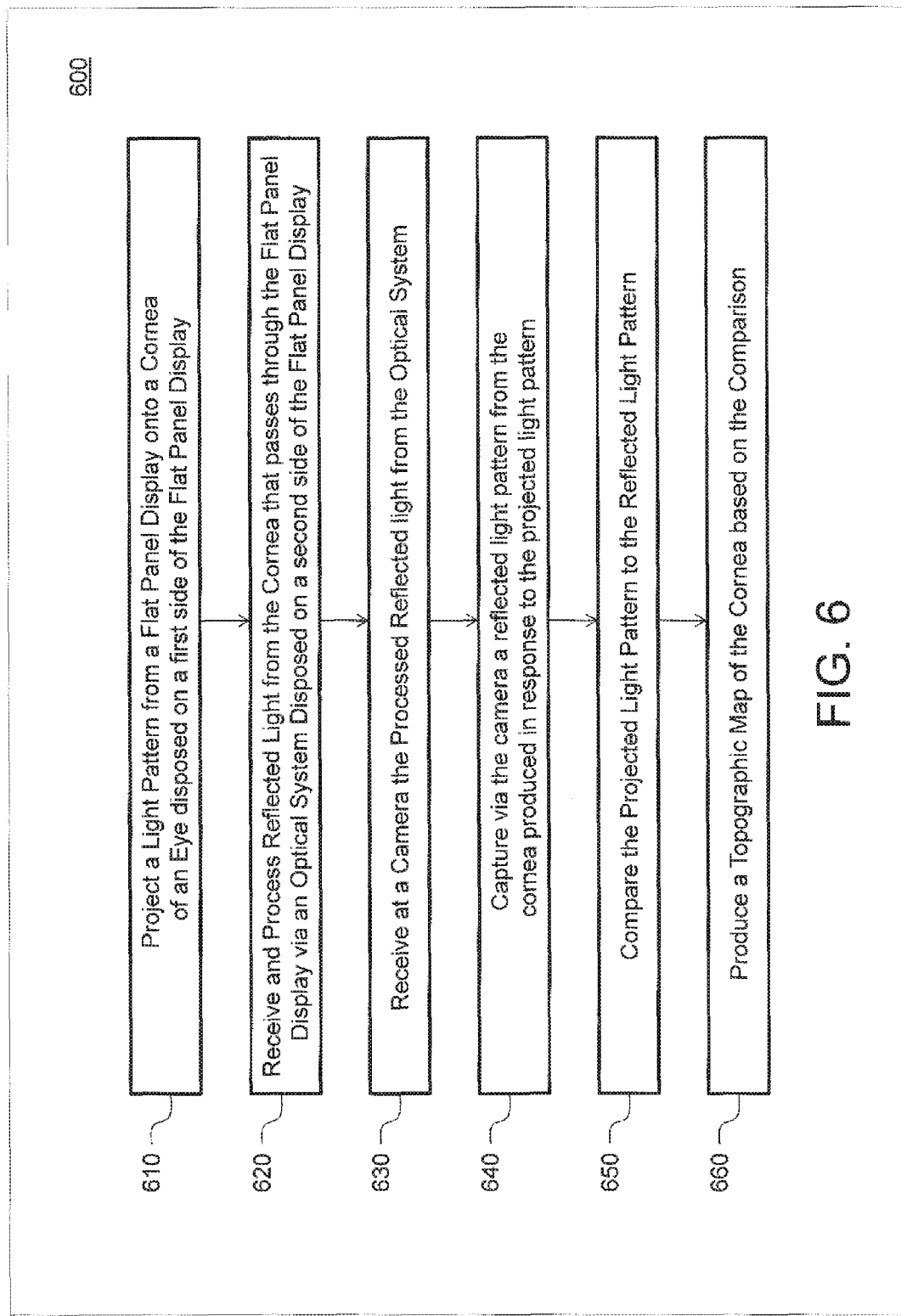
FIG. 6 is a flowchart of a method of corneal topography.

FIG. 6 is a flowchart of a method 600 of corneal topography. Method 600 may be performed by system 1000.

An operation 610 includes projecting a light pattern from a flat panel display onto a cornea of an eye disposed on a first side of the flat panel display.

An operation 620 includes receiving and processing reflected light from the cornea that passes through the flat panel display via an optical system disposed on a second side of the flat panel display. When system 1000 is employed, this may include passing reflected light from the cornea which passes through a transparent flat panel display.

An operation 630 includes receiving at a camera the processed reflected light from the optical system.

An operation 640 includes capturing via the camera a reflected light pattern from the cornea produced in response to the projected light pattern.

An operation 650 includes comparing the projected light pattern to the reflected light pattern. In some embodiments, this may be done by comparing the reflected light pattern to an idealized expected reflected light pattern which would be produced by the projected light pattern in the case of a model or idealized corneal surface. In particular, operation 650 may include comparing locations and/or shapes of reflected light spots to those expected for a standard or model cornea.

An operation 660 includes producing a topographic map of the cornea based on the comparison performed in operation 650.

Figure 7:
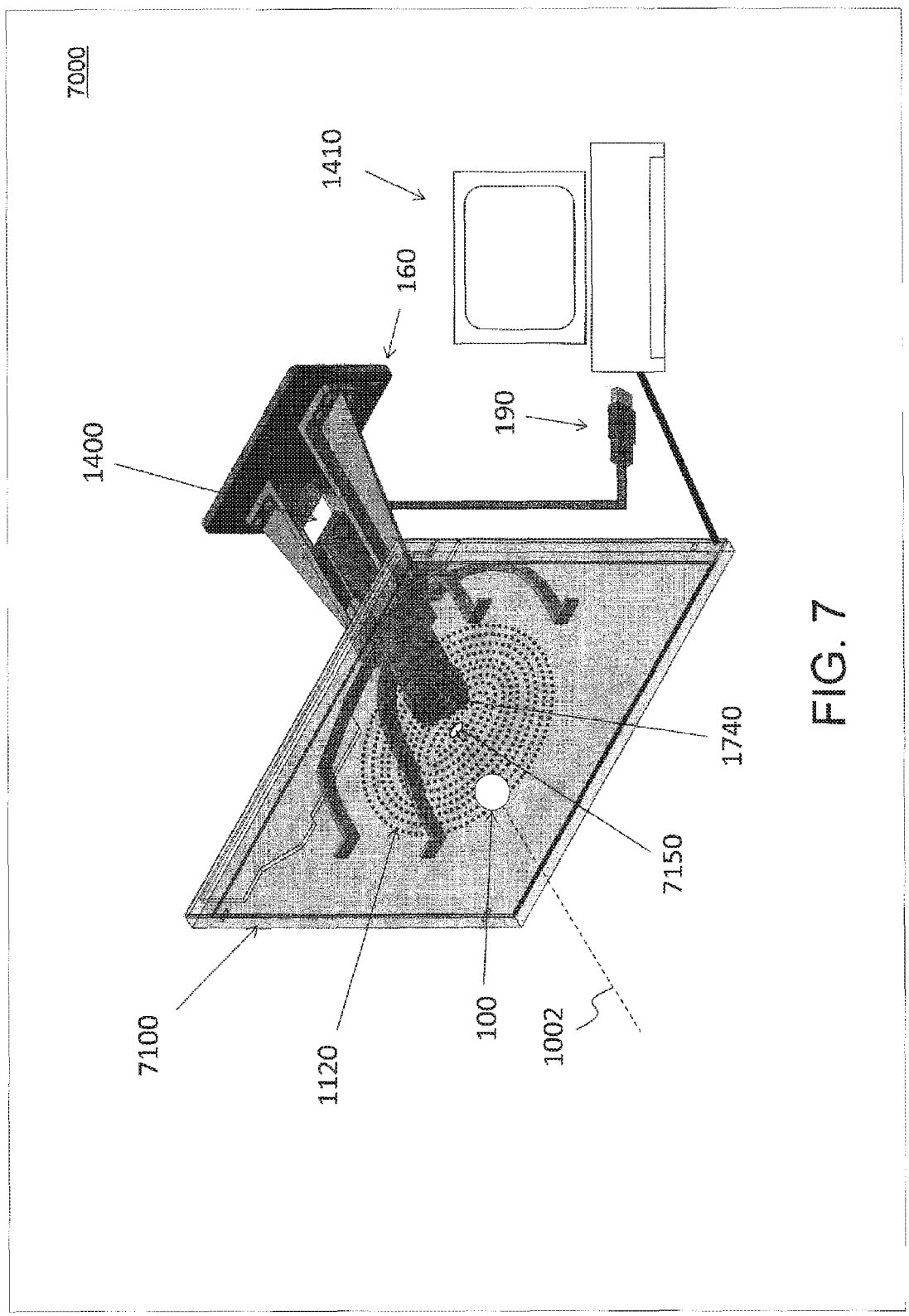
FIG. 7 illustrates a perspective view of a second embodiment of a system for corneal topography of an eye.

FIG. 7 illustrates a perspective view of a second embodiment of a system 7000 for corneal topography of an eye. System 7000 is constructed similarly to, and operates similarly to, system 1000 described above in detail, so only differences therebetween will be discussed.

System 7000 includes a flat panel display 7100 which has an aperture 7150 passing therethrough, wherein the reflected light from the cornea passes through aperture 7150 to optical system 1700. Accordingly, flat panel display 7100 need not be transparent. In various embodiments, flat panel display 7100 may comprise a liquid crystal display (LCD) device, an organic light emitting diode (OLED) display device, or other suitable display device.

Figure 8:
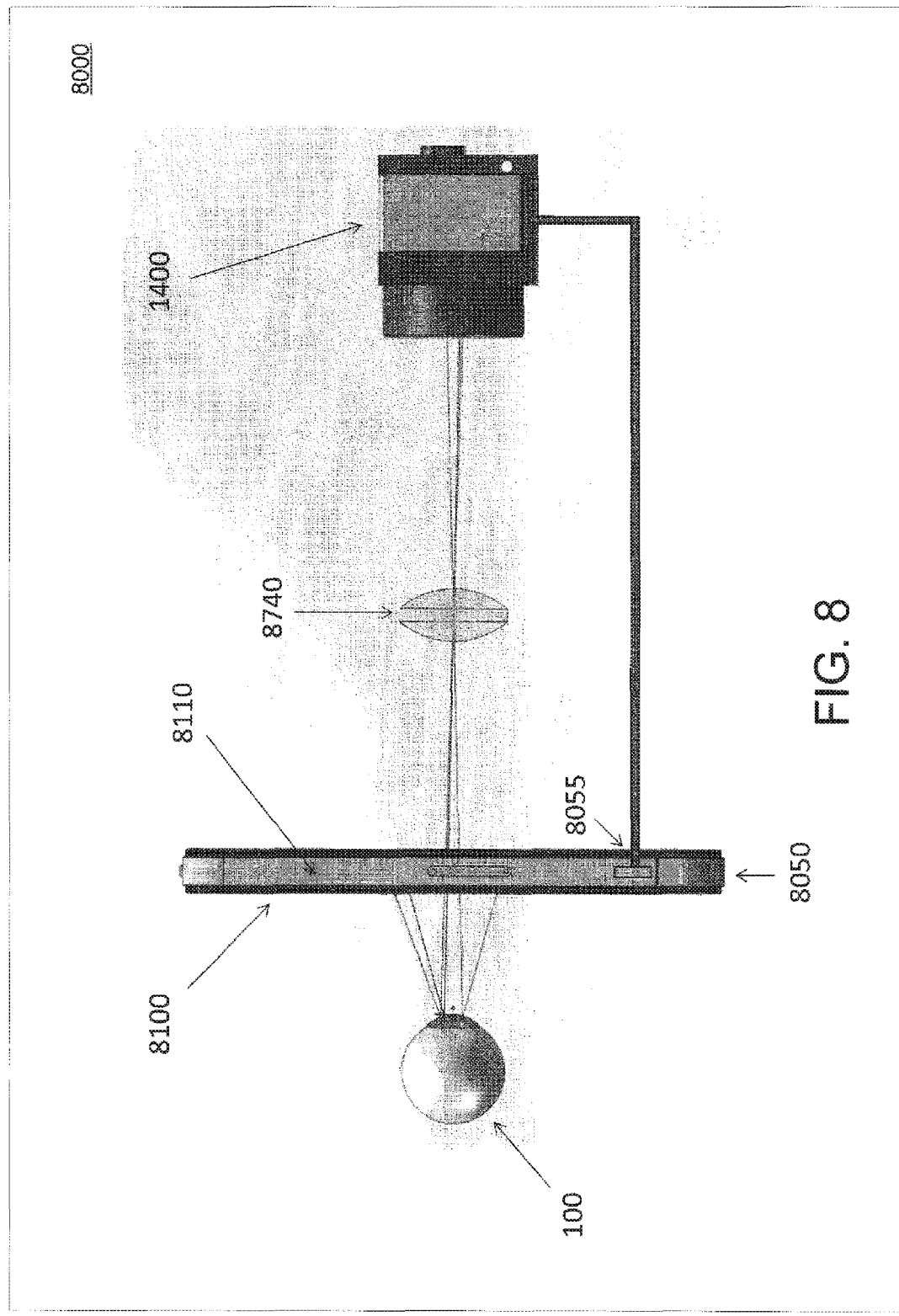
FIG. 8 illustrates a side view of a third embodiment of a system for measuring corneal topography of an eye.
Figure 9:
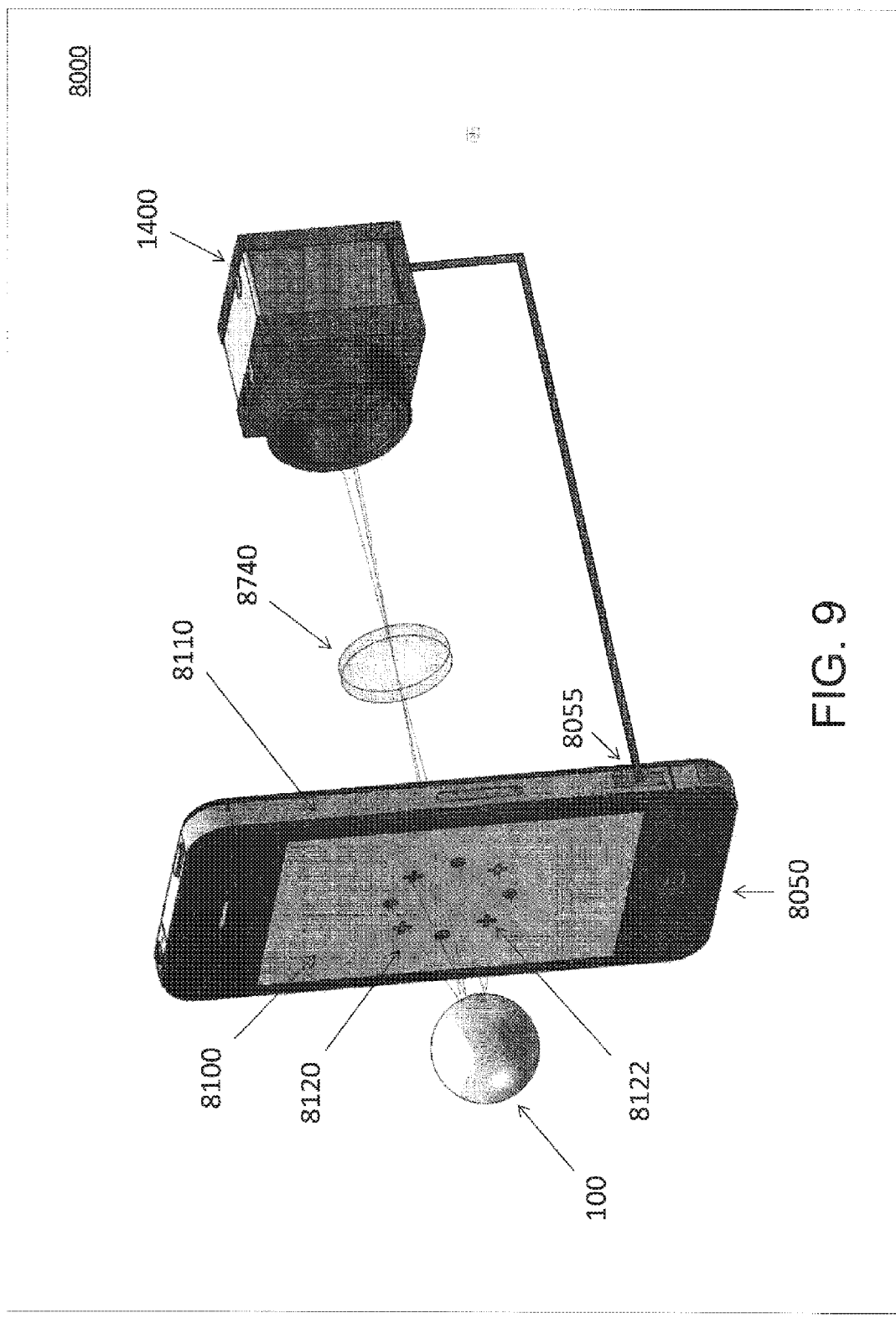
FIG. 9 illustrates a perspective view of the third embodiment of a system for measuring corneal topography of an eye.

FIG. 8 illustrates a side view of a third embodiment of a system 8000 for measuring corneal topography of an eye. FIG. 9 illustrates a perspective view of system 8000. System 8000 is constructed similarly to, and operates similarly to, system 1000 described above in detail, so only differences therebetween will be discussed.

System 8000 includes a portable computing device 8050 with housing 8110 and flat display panel 8100. In some implementations, portable computing device 8050 may comprise a smart phone or a tablet device. In some implementations, flat panel display 8100 may be a touchscreen. In some implementations, flat panel display 8100 may be a transparent LCD display, similarly to flat panel display 1100. In some implementations, flat panel display 8100 may have an aperture passing therethrough, wherein the reflected light from the cornea of eye 100 passes through the aperture to optical system 1700. In some embodiments, portable computing device 8050 may include one or more processor(s) and associated memory, which may include volatile memory and nonvolatile memory. Portable computing device 8050 may include an operating system, executable code, a user interface (e.g., keyboard, mouse, trackball, touchscreen, etc.), and other elements which may be found in smart phones and/or tablets, such as a wireless communications transceiver, a power supply, one or more data connectors 8055, front and/or rear facing cameras, etc.

Also, in system 8000, the optical system is simplified to comprise a single lens 8740. In portable computing device 8050, flat panel display 8100 is connected to housing 8110 and configured to display a light pattern 8120 thereon and to project light pattern 8120 onto the cornea of eye 100 which disposed on a first side of flat panel display 8100 and portable computing device 8050. Camera 1400 is disposed on a second side of flat panel display 8100 and portable computing device 8050.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Other variations are within the concept, scope, or spirit of the present invention. While the invention is susceptible to various modifications and alternative constructions, certain illustrated embodiments of the invention are shown in the drawings, and have been described above in an exemplary form with a certain degree of particularly. Those of ordinary skill in the art will understand, however, that the embodiments are provided by way of example only, and that various variations can be made without departing from the spirit or scope of the invention. Thus, there is no intention to limit the invention to the specific form or forms disclosed. Rather, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. An apparatus, comprising:
a flat panel display having a plurality of pixels and configured to display a light pattern formed by illumination of some of the pixels and to project the light pattern onto a cornea of an eye disposed on a first side of the flat panel display;
an optical system disposed on a second side of the flat panel display, the optical system being configured to receive and process reflected light from the cornea that passes through the flat panel display from the cornea to the optical system; and
a camera configured to receive the processed reflected light from the optical system and to capture therefrom a reflected light pattern from the cornea produced in response to the projected light pattern.

2. The apparatus of claim 1, further comprising: one or more processors configured to execute an algorithm to compare the projected light pattern to the reflected light pattern from the cornea, and to produce a topographic map of the cornea based on a result of the comparison.

3. The apparatus of claim 1, wherein the flat panel display is a transparent flat panel display, and wherein the reflected light from the cornea passes through the transparent flat panel display to the optical system.

4. The apparatus of claim 1, wherein the flat panel display has an aperture passing therethrough, and wherein the reflected light from the cornea passes through the aperture to the optical system.

5. The apparatus of claim 1, wherein the projected light pattern comprises a pattern of projected light spots and the reflected light pattern from the cornea comprises a pattern of reflected light spots.

6. The apparatus of claim 5, wherein the projected light spots are colored light spots, and wherein various projected light spots have different colors to facilitate association of the reflected light spots with the projected light spots from which they were generated.

7. The apparatus of claim 6, wherein the apparatus is configured to dynamically adjust the colors of the projected light spots to facilitate association of the reflected light spots with the projected light spots from which they were generated.

8. The apparatus of claim 5, wherein the projected light spots each have a size and shape, and wherein at least one of the size and shape of at least two of the projected light spots differ from each other to facilitate association of the reflected light spots with the projected light spots from which they were generated.

9. The apparatus of claim 8, wherein the apparatus is configured to dynamically adjust at least one of the size and shape of the projected light spots to facilitate association of the reflected light spots with the projected light spots from which they were generated.

10. The apparatus of claim 5, wherein the apparatus is configured to dynamically adjust a local density of the projected light spots to facilitate association of the reflected light spots with the projected light spots from which they were generated to facilitate production of the topographic map of the cornea.

11. A method, comprising:
providing a flat panel display having a plurality of pixels;
projecting a light pattern, formed by illumination of some of the pixels of the flat panel display, from the flat panel display onto a cornea of an eye disposed on a first side of the flat panel display;
receiving and optically processing reflected light from the cornea that passes through the flat panel display via an optical system disposed on a second side of the flat panel display;
receiving at a camera the optically processed reflected light from the optical system;
capturing from processed reflected light via the camera a reflected light pattern from the cornea produced in response to the projected light pattern;
comparing the projected light pattern to the reflected light pattern from the cornea; and
producing a topographic map of the cornea based on a result of the comparison.

12. The method of claim 11, wherein the flat panel display is a transparent flat panel display, the method further comprising passing the reflected light from the cornea through the transparent flat panel display to the optical system.

13. The method of claim 11, wherein the flat panel display has an aperture passing therethrough, the method further comprising passing the reflected light from the cornea through the aperture to the optical system.

14. The method of claim 11, wherein the projected light pattern comprises a pattern of projected light spots and the reflected light pattern from the cornea comprises a pattern of reflected light spots.

15. The method of claim 14, wherein the projected light spots are colored light spots, and wherein various projected light spots have different colors to facilitate association of the reflected light spots with the projected light spots from which they were generated.

16. The method of claim 15, further comprising: dynamically adjusting the colors of the projected light spots to facilitate association of the reflected light spots with the projected light spots from which they were generated.

17. The method of claim 14, wherein the projected light spots each have a size and shape, and wherein at least one of the size and shape of at least two of the projected light spots differ from each other to facilitate association of the reflected light spots with the projected light spots from which they were generated.

18. The method of claim 17, further comprising: dynamically adjusting at least one of the size and shape of the projected light spots to facilitate association of the reflected light spots with the projected light spots from which they were generated.

19. The method of claim 18, further comprising: dynamically adjusting a local density of the projected light spots to facilitate association of the reflected light spots with the projected light spots from which they were generated to facilitate production of the topographic map of the cornea.

20. An apparatus, comprising:
a portable computing device, comprising:
a housing;
a flat panel display having a plurality of pixels and connected to the housing and configured to display a light pattern thereon formed by illumination of some of the pixels and to project the light pattern onto a cornea of an eye disposed on a first side of the flat panel display, and
one or more processors disposed within the housing of the portable computing device;

an optical system disposed on a second side of the transparent flat panel display, configured to receive and process reflected light from the cornea that passes through the flat panel display; and a camera configured to receive the processed reflected light from the optical system and to capture therefrom a reflected light pattern from the cornea produced in response to the projected light pattern, wherein the one or more processors are configured to receive image data from the camera and to process the image data to produce a topographic map of the cornea.

21. The apparatus of claim 20, wherein the portable computing device comprises one of a smart phone and a tablet computer.

22. The apparatus of claim 21, wherein the one of the smart phone and the tablet computer includes the flat panel display.

23. The apparatus of claim 22, wherein the flat panel display is a transparent flat panel display, and wherein the reflected light from the cornea passes through the transparent flat panel display to the optical system.

24. The apparatus of claim 22, wherein the flat panel display has an aperture passing therethrough, and wherein the reflected light from the cornea passes through the aperture to the optical system.

* * * * *